United States Patent
Brunerie et al.

(10) Patent No.: US 10,670,525 B2
(45) Date of Patent: Jun. 2, 2020

(54) PORTABLE DEVICE FOR CONTROLLING AN ALCOHOLIC BEVERAGE THROUGH A CONTAINER, A SYSTEM AND A METHOD ASSOCIATED THERETO

(71) Applicants: Pernod Ricard, Paris (FR); CNRS—Direction de l'Innovation et des Relations avec les Entreprises (DIRE), Paris (FR); UNIVERSITE DE BORDEAUX, Bordeaux (FR); Institut Polytechnique de Bordeaux, Talence (FR)

(72) Inventors: Pascal Brunerie, Santeny (FR); Katia Gouret, Les Metairies (FR); Benoit Fil, Louzac (FR); Stephane Verger, Cognac (FR); Jean-Luc Bruneel, Saint Selve (FR); Francois Guillaume, Villenave D'Ornon (FR); Caroline Bruneel Delhaye, Saint Selve (FR)

(73) Assignees: PERNOD RICARD, Paris (FR); CNRS—DIRECTION DE L'INNOVATION ET DES RELATIONS AVEC LES ENTREPRISES (DIRE), Paris (FR); Universite de Bordeaux, Bordeaux (FR); INSTITUT POLYTECHNIQUE DE BORDEAUX, Talence (FR)

( * ) Notice: Subject to any disclaimer, the term of this patent is extended or adjusted under 35 U.S.C. 154(b) by 25 days.

(21) Appl. No.: 15/884,721

(22) Filed: Jan. 31, 2018

(65) Prior Publication Data

US 2018/0149592 A1 May 31, 2018

Related U.S. Application Data

(63) Continuation of application No. PCT/FR2016/051971, filed on Jul. 28, 2016.

(30) Foreign Application Priority Data

Jul. 31, 2015 (FR) ...................................... 15 57433

(51) Int. Cl.
*G01J 3/30* (2006.01)
*G01N 21/64* (2006.01)
(Continued)

(52) U.S. Cl.
CPC ............. *G01N 21/64* (2013.01); *G01N 21/27* (2013.01); *G01N 21/278* (2013.01);
(Continued)

(58) Field of Classification Search
CPC ...... G01N 21/64; G01N 21/645; G01N 21/27; G01N 33/14; G01N 33/146; G01N 2021/6421; G01J 3/4406
See application file for complete search history.

(56) References Cited

U.S. PATENT DOCUMENTS

| 2004/0000653 A1* | 1/2004 | Nordlund ............... G01N 21/31 250/573 |
| 2007/0023521 A1 | 2/2007 | Wildey et al. |

(Continued)

FOREIGN PATENT DOCUMENTS

| WO | 2002/033404 | 4/2002 |
| WO | 2005/001451 | 1/2005 |
| WO | 2014/184506 | 11/2014 |

OTHER PUBLICATIONS

International Search Report for International Application PCT/FR2016/051971, dated Jan. 9, 2017.

*Primary Examiner* — Tarifur R Chowdhury
*Assistant Examiner* — Jonathon Cook
(74) *Attorney, Agent, or Firm* — Burris Law, PLLC

(57) ABSTRACT

The present disclosure provides a portable device for controlling an alcoholic beverage that includes a single light source emitting a monochromatic excitation light beam of a wavelength between 350 and 650 nanometers, a beam splitter to reflect the light beam, a focus and collection lens,
(Continued)

and a positioning device to orient the light beam along a direction substantially normal to an outer surface of the container. The positioning device positions the outer surface of the container at a predetermined distance from the focus lens. The device includes a filtering device for filtering fluorescence radiation captured by the focus lens to eliminate wavelengths shorter than or equal to the wavelength of the light beam. A spectrometer module produces a signal corresponding to the measured spectrum of the fluorescence radiation and an analysis module compares the measured spectrum to a reference spectrum.

12 Claims, 4 Drawing Sheets

(51) Int. Cl.
  *G01N 33/14*  (2006.01)
  *G01N 21/27*  (2006.01)
(52) U.S. Cl.
  CPC ....... *G01N 33/146* (2013.01); *G01N 21/6486* (2013.01); *G01N 2021/6421* (2013.01); *G01N 2021/6497* (2013.01); *G01N 2201/0221* (2013.01)

(56) References Cited

U.S. PATENT DOCUMENTS

| | | | |
|---|---|---|---|
| 2011/0184681 A1* | 7/2011 | Augustine | G01N 22/00 702/75 |
| 2011/0292376 A1* | 12/2011 | Kukushkin | G01J 1/58 356/73 |
| 2015/0009490 A1 | 1/2015 | Poteet et al. | |

* cited by examiner

PORTABLE DEVICE FOR CONTROLLING AN ALCOHOLIC BEVERAGE THROUGH A CONTAINER, A SYSTEM AND A METHOD ASSOCIATED THERETO

CROSS-REFERENCE TO RELATED APPLICATIONS

This application is a continuation of International Application No. PCT/FR2016/051971, filed on Jul. 28, 2016, which claims priority to and the benefit of FR 15/57433 filed on Jul. 31, 2015. The disclosures of the above applications are incorporated herein by reference.

FIELD

The present disclosure relates to the field of the authentication of a content such as a beverage, in particular an alcoholic beverage. More specifically, the present disclosure concerns a device and a method to authenticate a beverage through the walls of a container, more particularly when the container is a bottle.

BACKGROUND

The statements in this section merely provide background information related to the present disclosure and may not constitute prior art.

The production and marketing costs of the high-end alcoholic beverages, such as vintage wines and spirits, lead to high selling prices. These high prices generate, as often for the luxury products, fraud as well as acts of counterfeiting. Thus, there is regularly observed the appearance on the market of counterfeit bottles, that is to say having the external appearance of a genuine bottle, but filled with a beverage of much lower quality than the quality of the original product. This phenomenon of counterfeiting is particularly significant for high-end wines and spirits, such as cognac.

For economic, safety and brand image reasons, the concerned producers are vigorously fighting against these acts of fraud and counterfeiting. This struggle is reflected in particular in the manufacture of bottles including increasingly advanced anti-counterfeiting devices, aiming at preventing the exact reproduction of a bottle and/or its reuse.

However, counterfeiters also make constant efforts and are able to reproduce genuine bottles with such faithfulness that it becomes very difficult to distinguish a counterfeit bottle from a genuine bottle. In other cases, counterfeiters recover used genuine bottles, which are then filled with a non-genuine product.

In addition, this question of authentication arises in various places related to different actors in the distribution chain (resellers, distributors, etc.).

SUMMARY

The present disclosure provides a portable device for controlling an alcoholic beverage in an at least partially transparent container, including:
a single light source emitting a monochromatic excitation light beam having a wavelength between 350 and 650 nanometers;
a beam splitter oriented at 45° with respect to the direction of emission of the light source to reflect the excitation light beam;
a focus and collection lens;
a positioning device allowing to orient the light beam coming from the light source along a direction substantially normal to the outer surface of the container, the positioning device also allowing to position the outer surface of the container at a predetermined distance from the focus lens, the predetermined distance between the focus lens and the container is chosen so that the light beam is focused inside the container, at a distance from the wall of the container less than 1 millimeter, and in one form is less than 500 micrometers, the positioning device including a through opening for the passage of the light beam coming from the light source;
a filtering device for filtering the fluorescence radiation captured by the focus lens and transmitted by the beam splitter, so as to eliminate the wavelengths which are shorter than or equal to the wavelength of the light beam emitted by the light source;
a spectrometer module for producing a signal corresponding to the measured spectrum of the fluorescence radiation of the beverage; and
an analysis module for comparing the measured spectrum with a reference spectrum.

By using the fluorescence phenomenon, the device in accordance with the present disclosure allows reducing the power of the excitation light source with respect to known devices, particularly those using the Raman effect (the intensity of the light emitted in the fluorescence process is indeed about a million times more intense than the Raman scattering). The device in accordance with the present disclosure includes a single light source, which contributes to the simplicity and portability of the system. In addition, by being limited to wavelengths greater than 350 nanometers, the influence of water and ethanol molecules (very much predominating in concentration in an alcoholic beverage such as a wine or a spirit) is limited. Indeed, water and ethanol molecules do not absorb the light radiation for wavelengths which are greater than 200 nanometers. Furthermore, by providing an assembly called "reflection" assembly, the attenuation of the fluorescence radiation is limited. Moreover, the 180° angle of incidence between the emitted ray and the reflected fluorescence ray allows reducing the undesirable effects due to the wall of the container, since the traversed thickness will be relatively thin. Further, by providing a positioning device, the focus of the emitted beam will be at the desired location, without further adjustments. The repeatability and reproducibility of the measurements are thus enhanced.

In one form, the beam splitter is a dichroic filter, in particular a high-pass dichroic filter (relative to the wavelengths).

In another form, the filtering device includes a Notch-type band-stop filter and/or a high-pass filter (relative to the wavelengths).

In another form, the spectrometer module is linked to the filtering device via an optical fiber.

In another form, the positioning device includes a contact surface configured to be complementary to the outer surface of the container.

In another form, the device includes a display device allowing in particular to display the result of the comparison between the measured spectrum and the reference spectrum.

In another form, the device includes a casing which is secured to the positioning device.

In another form, the casing includes all the components of the device.

In another form, the positioning device is connected to the casing by a flexible connection, the focus lens being integrated to the positioning device, the flexible connection including an optical fiber for transmitting the light beams passing through the focus lens.

In another form, the analysis module and the display device are included in an appended portable device, such as a tablet computer or a mobile phone.

In another form, the device includes a connection to a remote database.

The present disclosure also concerns a system for controlling an alcoholic beverage, the system including a device as defined above and a database stored in a remote server of the device.

In one form, the database includes one or more reference spectrum/spectra that can be downloaded by the device.

The present disclosure further concerns a method for controlling an alcoholic beverage through an at least partially transparent container, the method including the steps of:

acquiring a fluorescence spectrum of the beverage through the wall of the container;

normalizing the profile of the spectrum measured with respect to the maximum intensity of the reference spectrum;

calculating a resemblance factor between the measured spectrum and the reference spectrum; and determining, according to the obtained value of the resemblance factor, whether the beverage is genuine.

The control method in accordance with the present disclosure has many advantages. Thanks to the step of normalizing the measured spectrum, for example with respect to the maximum intensity of the reference spectrum, the dispersions due to the temperature of the controlled content and to the variations in the characteristics of the container (in particular the dimensional characteristics) are avoided. This normalization step also allows collecting, with a low-power excitation source, a signal of sufficient quality to be correctly analyzed. In addition, the step of comparing the measured spectrum with the reference spectrum, which involves the calculation of a resemblance factor, involves very limited calculation capacity, which capacity is now available on a "smartphone" type mobile phone.

In one form, the fluorescence spectrum is acquired by using a source emitting a monochromatic beam of a wavelength comprised between 350 and 650 nanometers.

In another form, the resemblance factor is calculated over a predetermined wavelength range, for example a wavelength range between 550 and 650 nanometers.

In another form, the resemblance factor is calculated by the method called least squares method or by an algorithm of the Hausdorff algorithm type.

In another form, the beverage is determined to be non-genuine if the resemblance factor is greater than 20.

In another form, the reference spectrum is obtained from the measurement of the fluorescence spectrum measured on a sample of a plurality of genuine bottles.

In another form, the method includes a step of downloading the reference spectrum from a remote database.

In another form, the method is implemented using a device or a system as defined above.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 4b is a detail of FIG. 4a;

Figure 1:
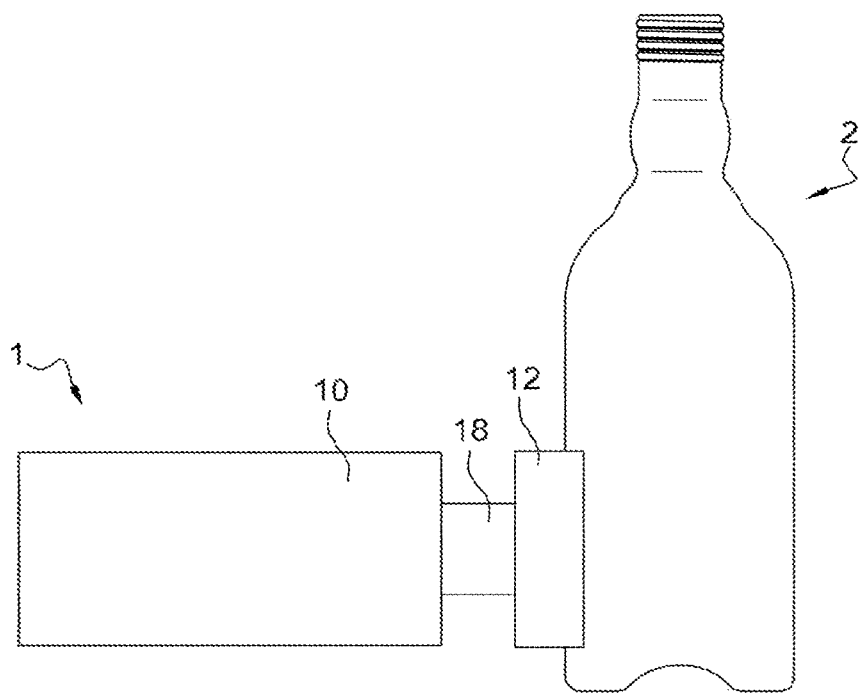
FIG. 1 is a side view of a device in use according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

FIG. 1 shows a portable device 1 in accordance with the present disclosure, and a container whose content is to be authenticated, for example a bottle 2 containing an alcoholic beverage. The device includes a casing 10, for example in a parallelepiped shape. The device 1 includes a device for positioning the bottle 2, or a positioning wedge 12. The wedge 12 forms a projection from one of the faces of the casing.

Figure 2:
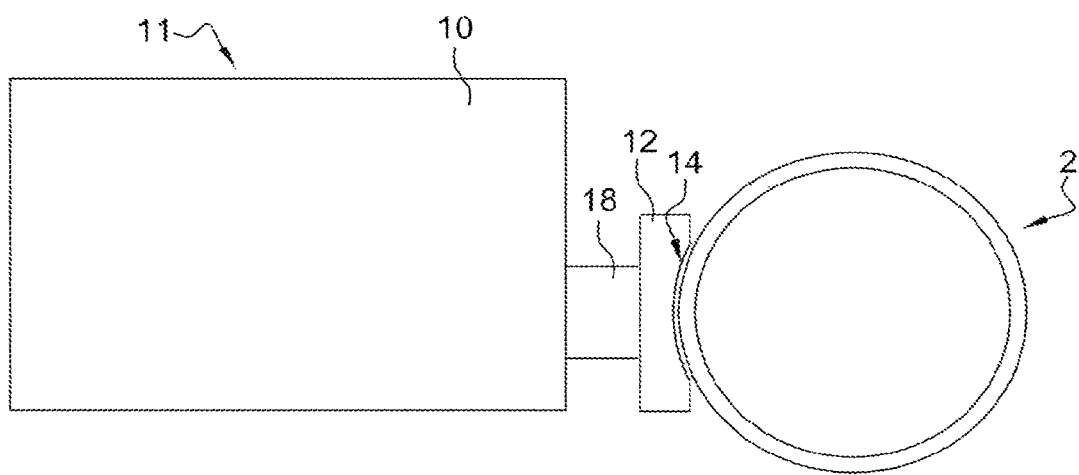
FIG. 2 is a top view of the device of FIG. 1.

As seen in FIG. 2, which is a top view of the device 1 and of the bottle 2, the wedge 12 has a contact surface 14 of complementary shape to the container. For example, the contact surface 14 thus has a concave shape adapted to the convex shape of the bottle 2.

Figure 3:
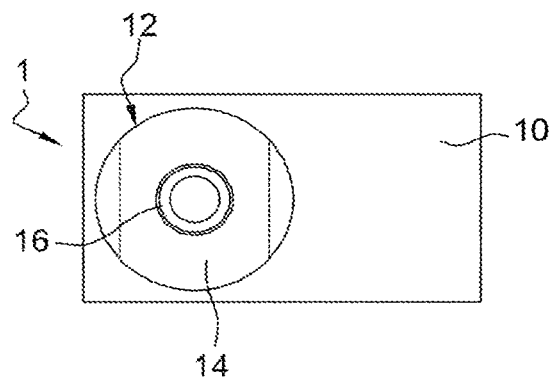
FIG. 3 is a front view of the device of FIG. 1.

As shown in FIG. 3, the wedge 12 has an opening 16 forming a passage allowing the light rays emitted by the device 1 to pass through the wedge 12. The wedge 12 is secured to the casing 10 via a support 18, this support 18 also having a through passage for the light rays emitted or received by the device 1.

Figure 4A:
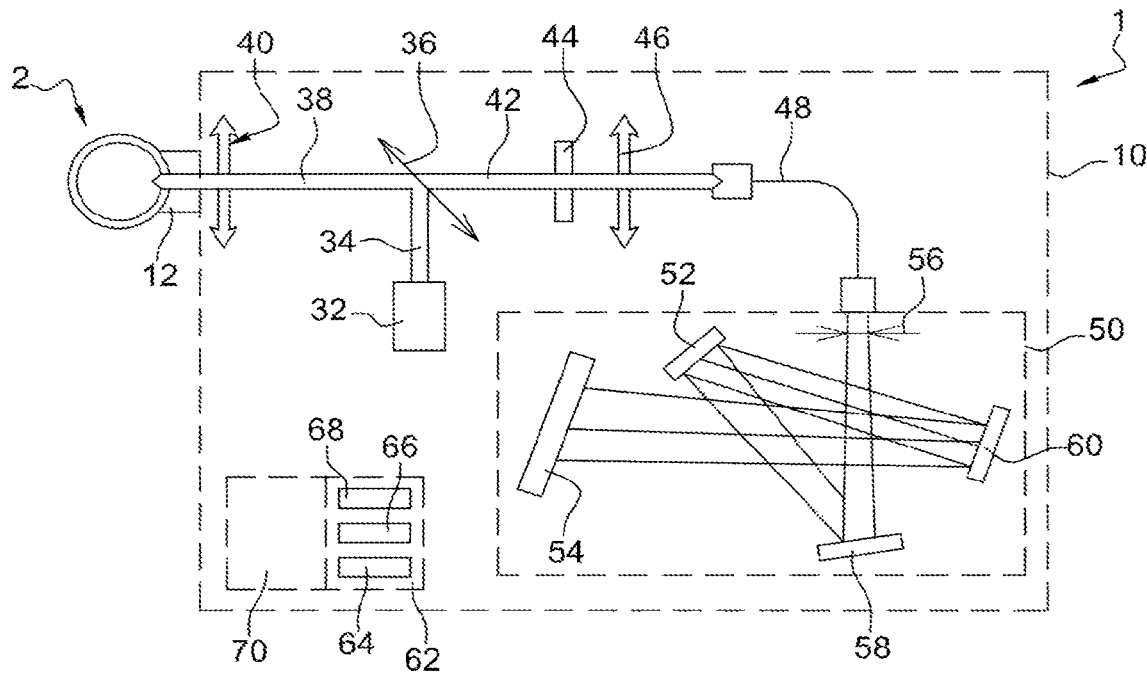
FIG. 4a is a block diagram of a device in accordance with the present disclosure.

FIG. 4a is a block diagram of the components of an exemplary device in accordance with the present disclosure. In this figure, for the sake of clarity, a bottle 2 is shown, and the casing 10 of the device 1 is shown in dotted lines. The device 1 represented in FIG. 4a includes a single excitation light source 32 emitting a monochromatic beam of a wavelength $\lambda_0$. For example, the light source 32 is a laser diode.

The wavelength $\lambda_0$ of the light source 32 is between 350 nanometers and 650 nanometers. This range allows obtaining that the emitted light beam generates a strong fluorescence emission of the molecules allowing to characterize the alcoholic beverage (that is to say the molecules other than those of water and ethanol). Moreover, in this range, the beam emitted by the light source 32 is only slightly attenuated by the glass of the bottle 2. Still in this range, the fluorescence emission of the content of the bottle 2 is only very weakly attenuated by the glass of the bottle 2.

The light beam 34 coming from the light source 32 is directed toward a beam splitter 36. The beam splitter 36, for example a dichroic filter, is oriented according to a 45° angle with respect to the direction of the light beam 34 emitted by the source 32. Thus, the beam emitted by the source 32 is reflected by the beam splitter 36 and the reflected beam 38 is directed toward a focus lens 40, for example an achromatic doublet lens. The focus lens 40 is located at a distance A from the bottle 2.

Figure 4B:
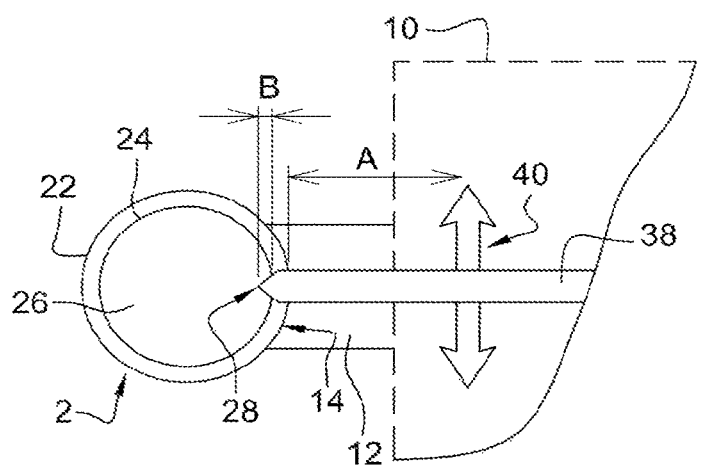

As seen in FIG. 4b, which represents a detail of FIG. 4a, the bottle 2, for example of a circular cross section, includes a wall delimited by an outer surface 22 and an inner surface 24. The bottle 2 contains a beverage 26 to be authenticated. The wedge 12 is in contact with the outer surface 22 of the bottle 2. As mentioned above, the wedge allows positioning the bottle 2 in such a way that the focus lens 40 is at a determined distance A from the outer surface 22 of the bottle. In addition, the wedge 12, by the shape of its contact surface 14, adapted to cooperate with the shape of the outer surface 22 of the bottle, allows positioning the bottle 2 in such a way that the light beam passing through the focus lens will be directed toward the outer surface 22 of the bottle 2 along a direction normal to this surface. For example, the contact surface 14 of the wedge 12 is of a concave shape and adapted to cooperate with the outer convex shape of the bottle 2. It should be noted in this respect that the wedge 12, and particularly the shape of the contact surface 14, will be adapted in the case where the container is not of a circular shape. Whatever the shape of the considered container, the shape of the contact surface 14 allows positioning the wedge 12 on the container so that the light beam passing through the focus lens 40 is directed toward the outer surface of the container along a direction normal to that surface. In order to easily adapt the positioning wedge 12 to each type of container, it will be of course possible to provide that the wedge 12 is removably attached to the casing 10. It may be further considered that the wedge 12 is connected to the casing via a flexible connection to facilitate the positioning of the wedge 12 on a container. In this case, the focus lens will be offset from the casing and secured to the positioning wedge 12. To this end, the flexible connection between the casing and the set formed by the positioning wedge 12 and by the focus lens will include an optical fiber to transmit the light beams from the casing to the focus lens and vice versa.

The spacing provided by the wedge 12 between the focus lens 40 and the bottle 2 will be determined so that the reflected beam 38 is focused inside the bottle 2, within the beverage 26, but as close as possible to the inner surface 24. FIG. 4b thus shows the focal point 28 located within the beverage 26 at a distance B from the wall of the bottle 2 (more precisely: at a distance B from the inner surface 24 of the wall of the bottle 2). The shorter the distance B, the more the path of the emitted beam and that of the fluorescence radiation is reduced, and the more the attenuation of these two signals is limited. The distance B will be advantageously less than 1 millimeter, and its value may be in the order of a few hundred micrometers or less.

The fluorescence signal 42 induced in the content of the bottle 2 by the light beam is collected by the focus lens 40, by retro-emission, and is directed toward the beam splitter 36. The beam splitter 36 allows the fluorescence signal, which is directed toward a spectrometer module 50, to pass.

Advantageously, the device 1 includes one or more filtering device(s) allowing to filter the fluorescence signal 42 before the latter is transmitted to the spectrometer module. The purpose of this filtering is in particular to eliminate the component of the signal collected by the focus lens 40 linked to the light beam emitted by the source 32. For this purpose, there is provided for example a band-stop filter 44 or "notch" filter. The interval of frequencies not transmitted by the band-stop filter will be close to the wavelength of the monochromatic light beam emitted by the source 32. The non-transmitted band will have for example a width of about 10 nanometers, and will be centered over a wavelength greater, by a few nanometers or less (for example 1 nanometer), to the wavelength $\lambda_0$ of the laser source.

It can further be provided that an additional high-pass type filtering (with respect to the wavelengths), is performed by the beam splitter 36. In this case, the beam splitter 36 is a high-pass type dichroic filter with a high cutoff slope (in particular an "edge"-type filter) which reflects the beam 34 toward the focus lens, and transmits the radiation emitted by the beverage and its container to the spectrometer module by eliminating the wavelengths which are shorter than a threshold value corresponding to the wavelength of the monochromatic beam emitted by the source 32 increased by about 10 nm.

In the example of FIG. 4a, the fluorescence signal 42, once filtered by the beam splitter 36 and by the stop-band filter 44, is directed toward a lens 46, for example an aspherical lens of a very short focal length. The beam transmitted by the lens 46 is directed toward one end of an optical fiber segment 48, the other end of this segment being linked to the spectrometer module 50. The optical fiber 48, due to its flexibility, allows enhancing placement of the components within the casing 10 and thus limiting the congestion therefrom. In addition, said optical fiber plays the role of a confocal hole and thus limits the amount of information transmitted and therefore analyzed. Thus, undesirable effects, particularly those related to the shape and thickness of the bottle or those related to outdoor lighting, can be reduced. Furthermore, the optical fiber also allows overcoming the astigmatism effect, which involves focus changes at the inlet of the spectrometer module according to the different wavelengths of the fluorescence radiation.

In one variant, the lens 46 may be replaced by a magnification lens.

The spectrometer module 50 includes a diffraction grating 52 allows directing the diffracted signal toward a sensor 54, for example a CCD-type sensor which has the advantage of not requiring cooling. For example, the diffraction grating 52 is a reflective diffraction grating. The signal entering the spectrometer module 50, via an input slot 56, is directed toward a first mirror 58, which is a convex mirror. The signal reflected by the diffraction grating 52 is directed toward a second planar-type mirror 60. The second mirror reflects the diffracted signal toward the sensor 54. In one variant, the set 52-58-60 can be replaced by a single concave diffraction grating allowing to improve the compactness of the device. In another variant, the set 52-58-60 can be replaced by a single diffraction grating operating in transmission.

The sensor 54 provides a signal corresponding to a fluorescence spectrum. This signal is transmitted from the spectrometer module 50 to an analysis module 62. The analysis module 62 includes in particular a storage unit 64, allowing to store in memory a signal coming from the spectrometer module. The storage unit 64 has a capacity allowing to store a signal obtained over a certain acquisition time, for example in the order of 150 milliseconds. The analysis module 62 further includes a calculation unit 66, allowing to determine whether the recorded signal corresponds to that of a genuine beverage. To this end, the calculation unit 66 performs in particular a comparison between the recorded signal and a reference signal, according to the method in accordance with the present disclosure, which will be described in more detail below. The reference signal may be previously stored in the storage unit 64 and/or downloaded or updated from a remote database. To this end, the analysis module 62 includes a communication unit 68, in particular of the wireless type.

The device finally includes a display device 70, allowing to display the result of the test. The display device 70 may include a display screen or any other means, such as a plurality of indicator lights (made for example with light-emitting diodes). For example, it is possible to provide that the result of the test is given according to one of two even three possibilities: "GOOD", "BAD" and possibly "DUBIOUS". In the case of a plurality of indicator lights, it will be thus possible to provide three different indicators (in particular of different colors), each corresponding indicator lighting up respectively according to one of the three possibilities mentioned above.

Figure 5:
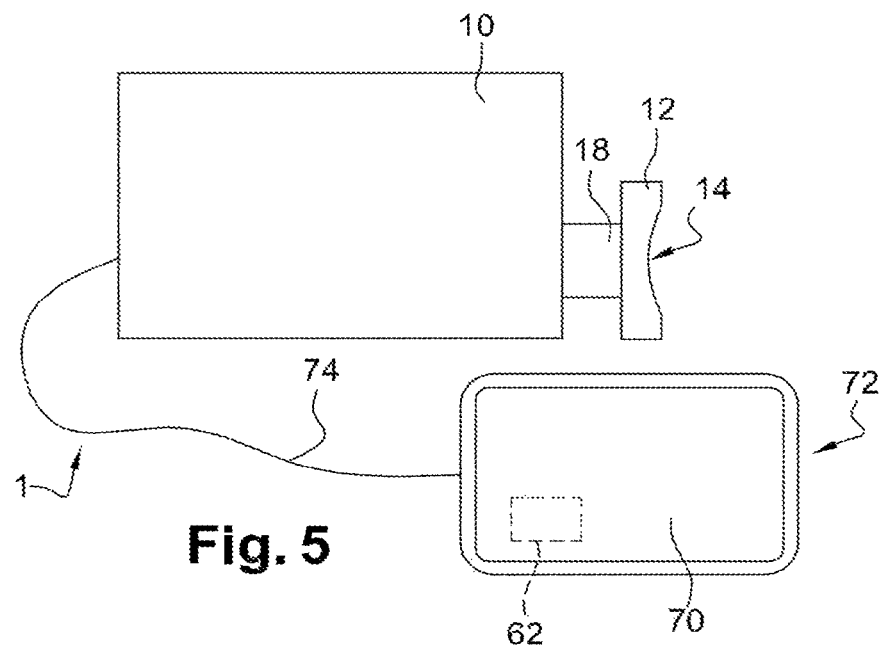
FIG. 5 shows a variant of a device in accordance with the present disclosure.

Alternatively, part or all of the analysis module 62 and/or of the display device 70 may be disposed in a casing distinct from the rest of the device. FIG. 5 represents one of the possible configurations, in which the analysis module 62 and the display device 70 are grouped together in an outer device, for example in the form of a portable device 72 such as a tablet computer or a mobile phone. In such a case, a wired or wireless-type digital connection 74 is provided between the casing 10 and the portable device 72. This connection allows connecting the spectrometer module 50, disposed in the casing 10, to the analysis module 62, located in the portable device 72.

Figure 6:
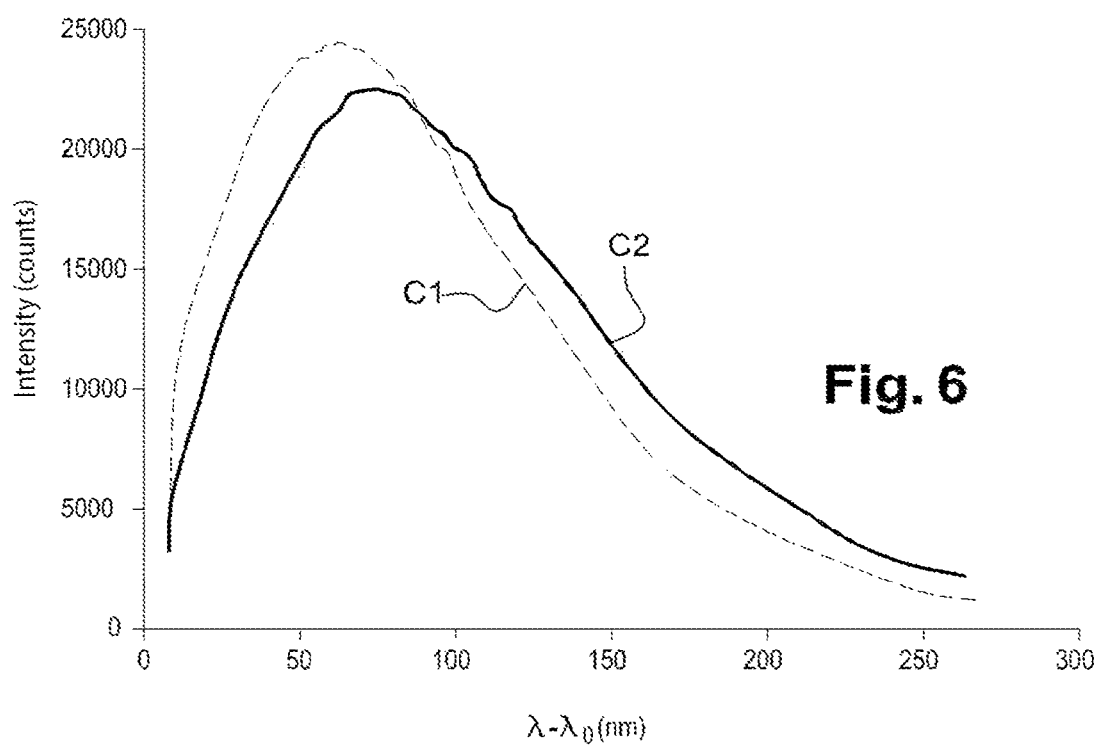
FIG. 6 is a plot corresponding to a reference spectrum in accordance with the present disclosure.
Figure 7:
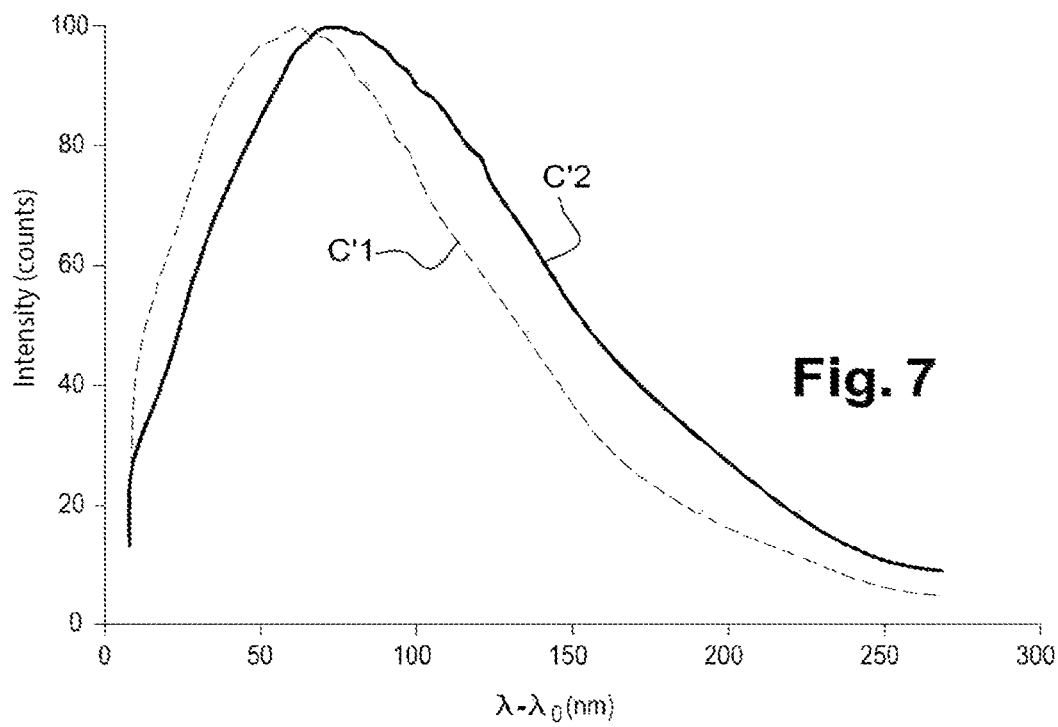
FIG. 7 is another plot corresponding to a measured spectrum in accordance with the present disclosure.

FIGS. 6 and 7 show spectrum examples obtained by the device in accordance with the present disclosure, respectively before and after implementation of a normalization step in accordance with the method according to the present disclosure.

FIG. 6 shows a curve C2 corresponding to a fluorescence spectrum obtained for a genuine cognac (contained in its original genuine bottle) and a curve C1 corresponding to a spectrum obtained for a non-genuine cognac (for example a counterfeit cognac). The two curves C1, C2 correspond to the output signal of the spectrometer module 50, and were obtained with a laser diode emitting a beam of a wavelength $\lambda 0$ close to 530 nanometers. It should be noted that the two curves have a maximum, corresponding to a wavelength of $\lambda 0+73$ nanometers for genuine cognac, and $\lambda 0+58$ nanometers for non-genuine cognac. In addition, the intensity of the maximum spectrum of non-genuine cognac is greater than the intensity of the maximum spectrum of genuine cognac.

FIG. 7 shows the two spectra of FIG. 6, after normalization with respect to the maximum intensity of the spectrum of the genuine cognac (taking as basis 100 the maximum intensity of the spectrum of the genuine cognac). This normalization leaves significant differences between the curve C'1 corresponding to the normalized profile of the spectrum of the non-genuine cognac and the curve C'2 corresponding to the normalized profile of the spectrum of the genuine cognac. As will be seen below, these differences are used by the device and the method in accordance with the present disclosure to allow the detection of non-genuine beverages through their container.

Figure 8:
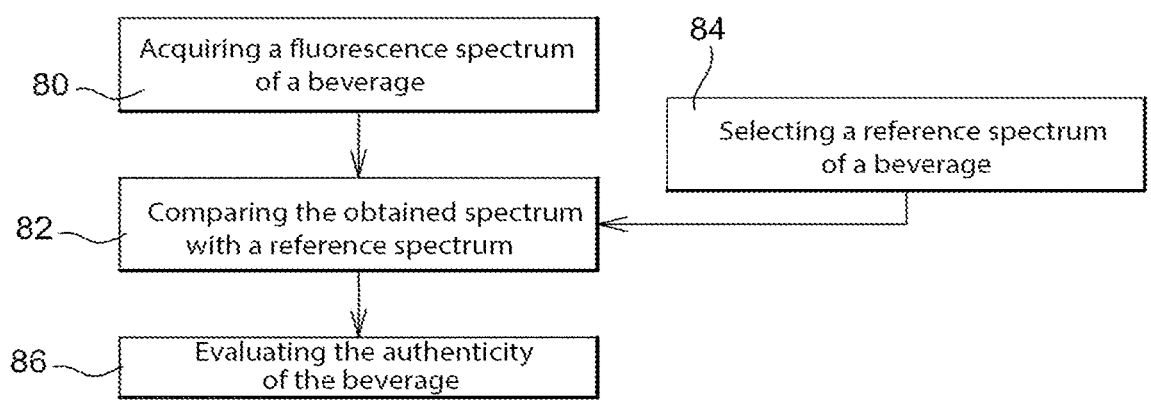
FIG. 8 is a diagram detailing the steps of a method in accordance with the present disclosure.

The control method in accordance with the present disclosure allowing the authentication of an alcoholic beverage is described hereinafter, in the context of an example applied to a cognac. The main steps of the method in accordance with the present disclosure are shown in FIG. 8. These steps can be carried out using a device in accordance with the present disclosure, for example the device 1 described above.

The method in accordance with the present disclosure includes a first step comprising acquiring a measured spectrum of the controlled beverage. This acquisition step 80 is carried out in particular by the spectrometer module 50 of the device 1.

The method then includes a comparison step 82 of the measured spectrum with a reference spectrum. This reference spectrum can be stored in a memory of the device 1, for example a memory of the storage unit 64, or can be downloaded from a remote database. Optionally, the method may include a step 84 of selecting the reference spectrum. This selection can be made among several reference spectra stored in memory, or among several reference spectra available in the remote database. This selection can be done automatically or to the user's request.

The comparison step 82 of the measured spectrum with the reference spectrum includes a sub-step comprising normalization of the measured spectrum, with respect to the maximum of the reference spectrum (or alternatively, with respect to the total intensity of the spectrum or with respect to the area under the spectrum). This normalization has several advantages. This allows in particular overcoming the effects of the temperature variations. The temperature is known to have a significant influence on the fluorescence phenomenon. But the inventors have discovered that a temperature change has a significant influence on the maximum intensity of the fluorescence spectrum, and a negligible influence in the form of the fluorescence spectrum profile. In other words, after normalization, spectra of the same beverage obtained at different temperatures are superimposable. Thus, the method in accordance with the present disclosure allows overcoming temperature variations during the collection of the fluorescence spectrum. Particularly, this allows taking into account the difference between the temperature at which the measured spectrum is collected and the temperature at which the reference spectrum has been created. In addition, the normalization of the measured spectrum allows overcoming the effects of the dispersions observed between each bottle of the same type. It is known that the same products on the same production line, two "identical" containers (such as glass bottles) will have dispersions, in particular dimensional dispersions (and therefore in the thickness). However, the greater the glass thickness, the more the beam emitted by the excitation source will be attenuated and also the more the emitted fluorescence radiation will be attenuated in the wall of the container. However, the inventors have discovered that this attenuation had a limited influence on the profile of the collected fluorescence spectrum, the attenuation having especially the effect of reducing the intensity of the spectrum. This influence on the profile of the spectrum is even more negligible if the length of the spectrum collected is less than 700 nanometers. It is therefore advantageous to limit the range of wavelengths used to implement the comparison step, for example between 550 and 650 nanometers. Thus, the method in accordance with the present disclosure allows overcoming thickness variations for the same container model.

The comparison step 82 of the measured spectrum with the reference spectrum includes a sub-step of determining a resemblance factor R between the curves corresponding respectively to a measured spectrum for a given beverage and to the reference spectrum corresponding to this beverage, for example the curves C'2 and C'1. This sub-step thus allows quantifying the resemblance between the measured spectrum and the reference spectrum. This factor R can be calculated for example by using the least squares method, according to the formula:

$$R_{1-2} = \sum_{i} \sqrt{(y_1(\lambda_i) - y_2(\lambda_i))^2}$$

wherein:

$y_1(\lambda_i)$ is the intensity of the measured spectrum (for example the curve C'1 of FIG. 7) for a wavelength equal to $\lambda_i$;

$y_2(\lambda_i)$ is the intensity of the reference spectrum (for example the curve C'2 of FIG. 7) for a wavelength equal to $\lambda_i$.

A zero value is thus obtained if the two spectra are completely identical. The higher the factor R, the more the compared spectra differ.

Of course, the resemblance factor can be calculated by using any other adapted algorithm such as, for example, the Hausdorff algorithm, according to the following formula:

$$R_{1-2} = \max\left\{\sup_{x_2 \in y_2} \inf_{x_1 \in y_1} \delta(x_1, x_2), \sup_{x_1 \in y_1} \inf_{x_2 \in y_2} \delta(x_1, x_2)\right\}$$

According to this formula, we calculate for each point $y_1(\lambda_i)$ of the spectrum $y_1(\lambda)$ its smallest distance to the points of the spectrum $y_2(\lambda)$. We then choose the greatest calculated distance noted $\delta_{max}(y_1, y_2)$. We then perform the same calculation for each point of the spectrum $y_2(\lambda)$ compared to the spectrum $y_1(\lambda)$ by choosing the greatest calculated distance $\delta_{max}(y_2, y_1)$. The resemblance factor or Hausdorff distance will then be the greatest value of these two maximum retained distances.

Whatever the method used, we obtain a zero R value if the two spectra are completely identical. Likewise, whatever the method used, the higher the factor R, the more the compared spectra differ.

The R value will be calculated on at least a hundred points, advantageously several hundred. For example, the number of points taken into account is in the order of 600.

The R value is used during the evaluation step 86 of the authenticity of the beverage. This step allows determining, based on the calculated value of the resemblance factor R whether the controlled bottle contains a genuine beverage or not. For example, the tested content will be declared "bad" if the resemblance factor R is greater than a predetermined value, for example equal to 20.

By implementing a comparison by calculation of a resemblance factor that involve limited calculation resources, the method in accordance with the present disclosure leads to a low calculation time. Advantageously, the measured spectrum will be collected and/or compared to the reference spectrum only over a limited range, for example between 550 and 650 nanometers. Restricting the field of analysis allows indeed excluding the possible residual luminescence of the glass and, as explained above, overcoming the thickness variations of the wall of the container. In addition, restricting the field of analysis allows further reducing the calculation time.

The device and the method in accordance with the present disclosure provides a portable device that is simple and quick to use. By normalizing the spectra with respect to the intensity maxima, both the dispersions related to the temperature of the content and to the shape of the container are avoided, and the calculation capacity is reduced.

In addition, the architecture and operation of the device allow limiting the maximum number of components. Thus, thanks to the choice of an excitation light source emitting at a determined wavelength, the use of filters is avoided in order to select a narrow band of wavelengths. By enhancing the intensity and the quality of the fluorescence signal, in particular by the choice of the wavelength of the laser source, it is possible to use a low power laser source, for example of a few milliwatts. This allows providing an autonomous device that can operate on batteries or cells, and avoiding the need for a cooling device. In this respect, it will be noted that the choice of a CCD-type sensor for the spectrometer module also avoids providing any cooling.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A portable device for controlling an alcoholic beverage stored in an at least partially transparent container, the portable device comprising:
a single light source emitting a monochromatic excitation light beam having a wavelength between 350 and 650 nanometers;
a beam splitter oriented at 45° with respect to the direction of emission of the light source to reflect the excitation light beam as a reflected beam;
a focus and collection lens to which is directed the reflected beam;
a casing;
at least one filter configured to filter fluorescence radiation captured by the focus and collection lens and transmitted by the beam splitter to eliminate wavelengths shorter than or equal to the wavelength of the light beam emitted by the light source;
a spectrometer configured to produce a signal corresponding to a measured spectrum of the fluorescence radiation of the beverage;
an analysis module configured to compare the measured spectrum to a reference spectrum;
wherein the portable device further includes a positioning wedge secured to the casing and forming a projection from a face of the casing,
said positioning wedge having a contact surface of complementary shape to an outer surface of the container that orients the reflected beam passing through the focus and collection lens along a direction normal to the outer surface of the container,
said positioning wedge being operable to position the outer surface of the container at a predetermined distance from the focus and collection lens such that the reflected beam is focused within the container and the distance from the wall of the container is less than 1 millimeter,
said positioning wedge including a through opening for passage of the reflected beam.

2. The device according to claim 1, wherein the predetermined distance is less than 500 micrometers.

3. The device according to claim 1, wherein the beam splitter is a dichroic filter or a high-pass dichroic filter.

4. The device according to claim 1, wherein the at least one filter includes at least one of a Notch-type band-stop filter and a high-pass filter.

5. The device according to claim 1, wherein the spectrometer is linked to the at least one filter via an optical fiber.

6. The device according to claim 1 further comprising a display device to display results of the comparison between the measured spectrum and the reference spectrum.

7. The device according to claim 1, wherein the light source, the beam splitter, the focus and collection lens, the at least one filter, the spectrometer, the analysis module, and a display device are disposed in the casing.

8. The device according to claim 1, wherein the positioning wedge is connected to the casing via a flexible connection, wherein the focus and collection lens are integrated to the positioning wedge and the flexible connection includes an optical fiber for transmitting the excitation light beams passing through the focus and collection lens.

9. The device according to claim 1, wherein the analysis module and a display device are in an appended portable device.

10. The device according to claim 1 further comprising a connection to a remote database.

11. A system for controlling an alcoholic beverage, the system comprising a device according to claim 10 and a database stored in a remote server of the device.

12. The system according to claim 11, wherein the database includes at least one reference spectra that can be downloaded by the device.

* * * * *